(12) United States Patent
Bar-Am et al.

(10) Patent No.: US 10,905,583 B2
(45) Date of Patent: Feb. 2, 2021

(54) DEVICE POSITIONABLE IN THE UTERINE CAVITY

(71) Applicant: OCON Medical Ltd., Modiin (IL)

(72) Inventors: Ilan Bar-Am, Jerusalem (IL); Ariel Weinstein, Modiin (IL)

(73) Assignee: OCON Medical Ltd., Modiin (IL)

( * ) Notice: Subject to any disclaimer, the term of this patent is extended or adjusted under 35 U.S.C. 154(b) by 357 days.

(21) Appl. No.: 15/521,629

(22) PCT Filed: Dec. 11, 2014

(86) PCT No.: PCT/IL2014/051086
§ 371 (c)(1),
(2) Date: Apr. 25, 2017

(87) PCT Pub. No.: WO2016/092531
PCT Pub. Date: Jun. 16, 2016

(65) Prior Publication Data
US 2017/0246027 A1  Aug. 31, 2017

(51) Int. Cl.
*A61F 6/14* (2006.01)
*A61F 6/00* (2006.01)
*A61M 31/00* (2006.01)

(52) U.S. Cl.
CPC ............ *A61F 6/142* (2013.01); *A61F 6/00* (2013.01); *A61F 6/14* (2013.01); *A61M 31/00* (2013.01)

(58) Field of Classification Search
CPC .. A61F 6/144; A61F 6/142; A61F 6/18; A61F 2/0004; A61F 2/0009; A61F 2/02; A61F 2/0031; A61F 2/005; A61F 6/00; A61F 6/14; A61K 9/0039; A61K 9/0036; A61M 31/002; A61M 31/00
See application file for complete search history.

(56) References Cited

U.S. PATENT DOCUMENTS

| 3,200,815 A | 8/1965 | Margulies |
| 3,397,691 A | 8/1968 | Majzlin |
| 3,405,711 A * | 10/1968 | Bakunin ............. A61F 6/142 128/839 |

(Continued)

FOREIGN PATENT DOCUMENTS

| CN | 201299698 | 9/2009 |
| CN | 202051882 | 11/2011 |

(Continued)

OTHER PUBLICATIONS

Notice of Reasons for Rejection dated Jan. 22, 2019 From the Japan Patent Office Re. Application No. 2017-531622. (5 Pages).

(Continued)

*Primary Examiner* — Ophelia A Hawthorne
(74) *Attorney, Agent, or Firm* — Greenberg Traurig, LLP

(57) ABSTRACT

An intrauterine device and method of delivering and using same are provided. The intrauterine device includes a wire having a portion capable of forming a three dimensional (3D) structure. The 3D structure is elastically deformable to a partially collapsed configuration via a crush force larger than a force applied thereto by a relaxed uterine cavity. The three dimensional structure is also capable of elastically contracting and expanding in response to contraction and expansion of the uterine cavity.

15 Claims, 9 Drawing Sheets

(56) References Cited

U.S. PATENT DOCUMENTS

| | | | | |
|---|---|---|---|---|
| 3,490,446 A | * | 1/1970 | Holanek | A61F 6/142 128/839 |
| 3,620,212 A | | 11/1971 | Fannon, Jr. et al. | |
| 3,757,775 A | * | 9/1973 | Marco | A61F 6/142 128/839 |
| 3,789,838 A | | 2/1974 | Fournier et al. | |
| 3,810,456 A | | 5/1974 | Karman | |
| 3,905,360 A | | 9/1975 | Zaffaroni | |
| 3,957,042 A | | 5/1976 | Krzaklewski et al. | |
| 3,973,560 A | | 8/1976 | Emmett | |
| 4,034,749 A | * | 7/1977 | Von Kesseru | A61F 6/144 128/833 |
| 4,111,196 A | | 9/1978 | Emmett | |
| 4,117,838 A | | 10/1978 | Hasson | |
| 4,708,134 A | * | 11/1987 | Wildemeersch | A61F 6/142 128/840 |
| 7,763,033 B2 | | 7/2010 | Gruber et al. | |
| 2005/0171569 A1 | | 8/2005 | Girard et al. | |
| 2006/0213522 A1 | | 9/2006 | Menchaca et al. | |
| 2008/0245371 A1 | | 10/2008 | Gruber | |
| 2008/0249534 A1 | | 10/2008 | Gruber et al. | |
| 2010/0300452 A1 | * | 12/2010 | Tal | A61F 6/18 128/839 |
| 2011/0271963 A1 | | 11/2011 | Bar-Am | |
| 2012/0316460 A1 | | 12/2012 | Stout | |
| 2014/0048074 A1 | * | 2/2014 | Tal | A61F 6/144 128/833 |
| 2014/0228943 A1 | | 8/2014 | Stigall et al. | |

FOREIGN PATENT DOCUMENTS

| | | |
|---|---|---|
| CN | 102355872 | 2/2012 |
| DE | 102004061823 | 7/2006 |
| FR | 1594885 | 6/1970 |
| JP | 52-056997 | 6/1976 |
| JP | 2002-523172 | 7/2002 |
| JP | 2010-526576 | 8/2010 |
| JP | 2014-524771 | 9/2014 |
| JP | 2018-504950 A | 2/2018 |
| WO | WO 00/12016 | 3/2000 |
| WO | WO 2008/139339 | 11/2008 |
| WO | 2010082197 A2 | 7/2010 |
| WO | WO 2010/082197 | 7/2010 |
| WO | WO 2016/092531 | 6/2016 |

OTHER PUBLICATIONS

Translation dated Jan. 7, 2019 of Notice of Reasons for Rejection dated Oct. 23, 2018 From the Japan Patent Office Re. Application No. 2017-531622. (4 Pages).
Translation dated Jan. 24, 2019 of Notice of Reasons for Rejection dated Jan. 22, 2019 From the Japan Patent Office Re. Application No. 2017-531622. (4 Pages).
Supplementary European Search Report and the European Search Opinion dated Aug. 2, 2018 From the European Patent Office Re. Application No. 14907677.0. (7 Pages).
Notification of the Need for Additional Materials dated Jan. 21, 2019 From the Eurasian Patent Organization, Eurasian Patent Office Re. Application No. 201791230 and Its Translation Into English. (2 Pages).
Search Report and Written Opinion dated Jan. 2, 2018 From the Intellectual Property Office of Singapore Re. Application No. 11201704381U. (9 Pages).
International Preliminary Report on Patentability dated Jun. 22, 2017 From the International Bureau of WIPO Re. Application No. PCT/IL2014/051086 . (8 Pages).
Notice of Reasons for Rejection dated Oct. 23, 2018 From the Japan Patent Office Re. Application No. 2017-531622. (6 Pages).
Notification of Office Action and Search Report dated Sep. 30, 2018 From the State Intellectual Property Office of the People's Republic of China Re. Application No. 201480083727.9. (7 Pages).
Translation dated Oct. 18, 2018 of Notification of Office Action dated Sep. 30, 2018 From the State Intellectual Property Office of the People's Republic of China Re. Application No. 201480083727. 9. (4 Pages).
Notice of Reasons for Rejection dated Oct. 23, 2018 From the Japan Patent Office Re. Application No. 2017-531622 and its Translation Into English. (9 Pages).
Notification of Office Action dated Mar. 13, 2019 From the State Intellectual Property Office of the People's Republic of China Re. Application No. 201480083727.9 and Its Translation Into English. (10 Pages).
Translation dated Nov. 14, 2018 of Notice of Reasons for Rejection dated Oct. 23, 2018 From the Japan Patent Office Re. Application No. 2017-531622. (4 Pages).
International Search Report and the Written Opinion dated Mar. 13, 2015 From the International Searching Authority Re. Application No.PCT/IL2014/051086.
Aguilar et al. "Physiological Pathways and Molecular Mechanisms Regulating Uterine Contractility", Human Reproduction Update, 16(6): 725-744, 2010.
Baker et al. "Minimum Intrauterine Pressure Required for Uterine Distention", Journal of the American Association of Gynecologic Laparoscopists, 5(1): 51-53, Feb. 1998.
Bradley "Ultrasound Interactive Case Study: Ring IUD", 4 P., Aug. 1998.
Delvin "Contraceptive Coils (IUDs)", Netdoctor, Retrieved From the Internet on Jul. 5, 2006.
FHI "Methods of Contraceptive Action. Mechanisms of the Contraceptive Action of Hormonal Methods and Intrauterine Devices (IUDs)", Family Health International, 8 P., 2006.
French et al. "Hormonally Impregnated Intrauterine Systems (IUSs) Versus Other Forms of Reversible Contraceptives as Effective Methods of Preventing Pregnancy", Cochrane Database of Systemic Reviews, 3: CD001776, 2004. Abstract.
INED "Births / Birth Control. What Are the Most Widely Used Contraceptive Methods Across the World?", Institute Nationale d'Etudes Demographiques, INED, Retrieved From the Internet on Nov. 16, 2006.
John Hopkins School "Background", Population Information Program, Center for Communication Programs, The John Hopkins School of Public Health, XXIII(5): Chap.1: Background, Population Reports, Series B, No. 6, 1 P., Dec. 1995.
John Hopkins School "Bleeding and Pain", Population Information Program, Center for Communication Programs, The John Hopkins School of Public Health, XXIII(5): Chap.2.5: Bleeding and Pain, Population Reports, Series B, No. 6, 2 P., Dec. 1995.
John Hopkins School "Developed Countries", Population Information Program, Center for Communication Programs, The John Hopkins School of Public Health, XXIII(5): Chap.6.2: Developed Countries, Population Reports, Series B, No. 6, 1 P., Dec. 1995.
John Hopkins School "Ectopic Pregnancies", Population Information Program, Center for Communication Programs, The John Hopkins School of Public Health, XXIII(5): Chap.2.9: Ectopic Pregnancies, Population Reports, Series B, No. 6, 2 P., Dec. 1995.
John Hopkins School "Effectiveness", Population Information Program, Center for Communication Programs, The John Hopkins School of Public Health, XXIII(5): Chap.2.3: Effectiveness, Population Reports, Series B, No. 6, 1 P., Dec. 1995.
John Hopkins School "Types of IUDs", Population Information Program, Center for Communication Programs, The John Hopkins School of Public Health, XXIII(5): Chap.2.1: Types of IUDs, Population Reports, Series B, No. 6, 1 P., Dec. 1995.
John Hopkins School "Worlwide Use of IUDs, 1995. Estimated Use Among Married Women of Reproductive Age", Population Information Program, Center for Communication Programs, The John Hopkins School of Public Health, XXIII(5): Table 2, Tables for IUDs—An Update, Series J, No. 45, 7 P., Dec. 1995.
K4Health "Evolution and Revolution: The Past, Present, and Future of Contraception", Contraception Report, K4Health, John Hopkins University, 10(6): 1-12, Feb. 2000. Abstract.
Kaufman "The Cost of IUD Failure in China", Studies in Family Planning, 24(3): 194-196, May-Jun. 1993. Abstract.

(56) References Cited

OTHER PUBLICATIONS

Keller "IUDs Block Fertilization", Family Health International, 16(2): 1-2, Winter 1996.
Lynch "History of the IUD", Baylor College of Medicine, Houston, TX, USA, ContraceptiveOnline, p. 1-17, Jan. 27, 2006.
Schering "Nova T 380", Patient Information Leaflet, Jan. 2005.
Smith "Contraceptive Concerns. Commentary on Medical News by A Practicing Physician", Medpundit, 32 P., Mar. 8, 2003.
Van Gestel et al. "Endometrial Wave-Like Activity in the Non-Pregnant Uterus", Human Reproduction Update, 9(2): 131-138, 2003.
Van Kets "Importance of Intrauterine Contraception", Contraception Today, Proceedings of the 4th Congress of the European Society of Contraception, p. 112-116, 1997.
WHO "The Intrauterine Device (IUD)—Worth Singing About", Progress in Reproductive Health Research, World Health Organization, WHO, 60: 1-8, 2002.
Wyoming Health Council "All About the Intrauterine Device (IUD)", Wyoming Health Council, 1 P., 2004.
Notification of the Need for Additional Materials dated Jun. 11, 2019 From the Eurasian Patent Organization, Eurasian Patent Office Re. Application No. 201791230 and Its Translation Into English. (2 Pages).
Notification of Office Action dated Jul. 3, 2019 From the State Intellectual Property Office of the People's Republic of China Re. Application No. 201480083727.9 and Its Summary in English. (5 Pages).
Translation dated Jul. 10, 2019 of Notification of Office Action dated Jul. 3, 2019 From the State Intellectual Property Office of the People's Republic of China Re. Application No. 201480083727.9. (7 Pages).
Examination Report dated Jan. 10, 2020 From the Australian Government, IP Australia Re. Application No. 2014413482. (6 Pages).
Communication Pursuant to Article 94(3) EPC dated Apr. 21, 2020 From the European Patent Office Re. Application No. 14907677.0. (5 Pages).
Search Report and Technical Report dated Feb. 17, 2020 From the Servico Publico Federal, Ministerio da Economia, Instituto Nacional da Propriedade Industrial, INPI do Brasil Re. Application No. BR112017011905-6 and Its Translation Into English. (8 Pages).
Notification About Necessity to Submit Additional Materials dated Nov. 19, 2019 From the Eurasian Patent Organization, Eurasian Patent Office Re. Application No. 201791230 and Its Translation Into English. (3 Pages).

* cited by examiner

DEVICE POSITIONABLE IN THE UTERINE CAVITY

RELATED APPLICATIONS

This application is a National Phase of PCT Patent Application No. PCT/IL2014/051086 having International filing date of Dec. 11, 2014, the contents of which are all incorporated by reference as if fully set forth herein in its entirety.

FIELD AND BACKGROUND OF THE INVENTION

The present invention relates to a device positionable in the uterine cavity and, more particularly, to an intrauterine device configured for preventing pregnancy or treating uterine related disorders such as menorrhagia.

An intrauterine device (IUD) is a small device which is implanted in the uterine cavity and can be used for birth control. There are two general types of contraceptive IUDs, Copper IUDs and hormonal IUDs.

Copper IUDs (e.g. Paragard) are the most commonly used IUDs. Copper IUDs force the uterus and fallopian tubes to produce a fluid that contains white blood cells, copper ions, enzymes, and prostaglandins which are toxic to sperm.

Hormonal IUDs (e.g. Mirena or Skyla), release a form of the hormone progestin. Hormonal IUDs prevent fertilization by damaging or killing sperm, preventing sperm migration into the uterus (by making the mucous viscous and sticky) and by preventing implantation and growth of the fertilized egg (by preventing thickening of the endometrium). Hormonal IUDs can also reduce menstrual bleeding and cramping.

Both copper and hormonal IUDs are effective at preventing pregnancy (hormonal IUDs might be slightly more effective than copper IUDs), however, both suffer from several inherent limitations. Copper IUDs may increase menstrual bleeding or cramps, while hormonal IUDs may lead to side effects similar to those caused by oral contraceptives, such as breast tenderness, mood swings, headaches, and acne. Hormonal IUDs may also increase the risk of ovarian cysts.

In addition to the above, both types of IUDs can also cause uterine wall perforations and are susceptible to expulsion. In about 1 out of 1,000 women, an IUD will lodge in, or perforate the uterus wall, typically during insertion. About 2 to 10 out of 100 IUDs are expelled from the uterus into the vagina during the first year. Expulsion is more likely when the IUD is inserted right after childbirth or in women who have not carried a pregnancy or are 20 years old or younger.

Another limitation of presently used IUDs is mal-position. An IUD which is not positioned correctly or migrates out of its optimal position during use can be less effective in preventing a pregnancy. If pregnancy does occur, the presence of the IUD increases the risk of miscarriage, particularly during the second trimester. Removal of the IUD at the beginning of the pregnancy still carries a risk for premature delivery.

Thus, it would be highly advantageous to have a uterine-implantable device which can be used to prevent pregnancy or treat uterine-related disorders while being devoid of the above limitations.

SUMMARY OF THE INVENTION

According to one aspect of the present invention there is provided an intrauterine device comprising a wire including a portion forming a three dimensional structure being elastically deformable to partially collapsed configuration via a crush force larger than a force applied thereto by a relaxed uterine cavity, the three dimensional structure being capable of elastically contracting and expanding in response to contraction and expansion of the uterine cavity.

According to further features in preferred embodiments of the invention described below, the crush force is at least 15 grams/cm$^2$ and no more than 60 grams/cm$^2$. Preferably, the intrauterine device is configured such that a crush force of about 15 grams/cm$^2$ partially collapses the roughly spherical three dimensional structure, while any additional crush force further collapses the device nearly completely flattens it at about 50-60 grams/cm$^2$ total crush force.

According to still further features in the described preferred embodiments the three dimensional structure is 12-20 mm in diameter, preferably 13 mm in diameter.

According to still further features in the described preferred embodiments the wire of the three dimensional structure is elastically linearizable via a pull force of 100-150 grams to a free end of the wire.

According to still further features in the described preferred embodiments the three dimensional structure is formed by at least two loops-like structures angled with respect to each other.

According to still further features in the described preferred embodiments the wire is 0.4-0.6 mm in diameter.

According to still further features in the described preferred embodiments the wire is made of Nitinol.

According to still further features in the described preferred embodiments the at least two loops-like structures are positioned at an angle of 80-100 degrees with respect to each other.

According to still further features in the described preferred embodiments each of the at least two loops-like structures is 12-14 mm in diameter.

According to still further features in the described preferred embodiments an angle between the at least two loops-like structures decreases when the three dimensional structure elastically contracts.

According to still further features in the described preferred embodiments at least one of the at least two loops-like structures elastically ovalizes when the three dimensional structure elastically contracts.

According to still further features in the described preferred embodiments the device further comprises beads attached to the wire.

According to still further features in the described preferred embodiments the beads are 1.5-6.0 mm in diameter.

According to still further features in the described preferred embodiments the beads are spaced apart along the wire forming the three dimensional structure.

According to still further features in the described preferred embodiments a portion of the beads freely slide upon the wire.

According to still further features in the described preferred embodiments the beads are made of copper.

According to still further features in the described preferred embodiments the beads include an active agent.

According to still further features in the described preferred embodiments the active agent is selected from the group consisting of a hormone, a tissue ablation agent, a chemical agent and pharmaceutical agent.

According to still further features in the described preferred embodiments the wire is coated with a material capable of releasing an active agent in the uterine cavity.

According to still further features in the described preferred embodiments the active agent is selected from the group consisting of a hormone, a tissue ablation agent, a chemical agent and pharmaceutical agent.

According to another aspect of the present invention there is provided a system for treating a uterine cavity comprising: (a) a wire including a portion forming a three dimensional structure being elastically deformable to partially collapsed configuration via a crush force larger than a force applied thereto by a relaxed uterine cavity, the three dimensional structure being capable of elastically contracting and expanding in response to contraction and expansion of the uterine cavity; and (b) a delivery guide for advancing the wire into the uterine cavity.

According to still further features in the described preferred embodiments the delivery guide maintains the wire in a linear configuration such that when advanced out of the delivery guide, the portion of the wire forms the three dimensional structure.

According to still further features in the described preferred embodiments the three dimensional configuration is formed by sequential wire looping as the portion of the wire is advanced out of the delivery guide.

According to still further features in the described preferred embodiments the system further comprises an imaging or lighting unit attachable to the delivery guide.

According to yet another aspect of the present invention there is provided a method of treating a uterine cavity comprising delivering an intrauterine device into the uterine cavity, the device including a wire having a portion forming a three dimensional structure being elastically deformable to a partially collapsed configuration via a crush force larger than a force applied thereto by a relaxed uterine cavity, the three dimensional structure being capable of elastically contracting and expanding in response to contraction and expansion of the uterine cavity.

According to still further features in the described preferred embodiments the wire includes an active agent selected from the group consisting of a birth control agent, a drug, a tissue ablation agent, a chemical agent and a pharmaceutical agent.

The present invention successfully addresses the shortcomings of the presently known configurations by providing an intrauterine device configured for maximum stability in the uterine cavity and minimum uterine wall irritation (maximum compliance) and user discomfort.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

The present invention is of an implantable device which can be used to prevent pregnancy or treat uterine-related disorders. Specifically, the present invention relates to an intrauterine device capable of releasing an active agent suitable for preventing pregnancy, release hormones for menopausal treatment, treatment of intrauterine infections or treating endometrial disorders and myometrial disorders.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Figure 1A:
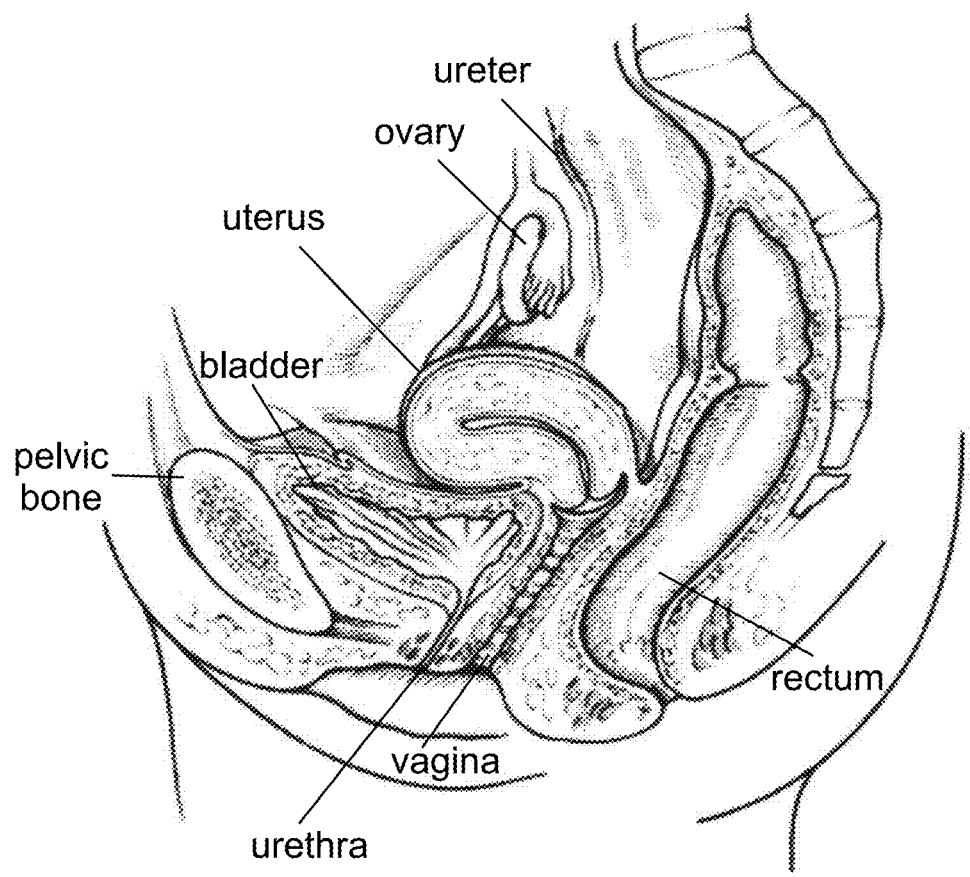
FIGS. 1a-b illustrate a uterine cavity in its relaxed state (FIG. 1a), and a prior art T-shaped IUD disposed within a relaxed uterine cavity (FIG. 1b).

In its relaxed state, the cavity of the uterus is a mere slit having substantially no volume (FIG. 1a). During uterine contractions, the uterine walls relax and contract upon each other. When relaxed, the uterine walls exert an inward force of 10 mmHg (about 13.5 grams $cm^2$), however, under contractions, inward forces exerted by the uterine walls can rise to as much as 50-60 mmHg (about 67-82 grams/$cm^2$) and higher (Gestel et al. Human Reproduction Update, Vol. 9, No. 2 pp. 131-138, 2003).

The overall design of presently used IUDs has not changed in decades since it is dictated by the anatomical space constraints of the relaxed uterus. Thus, the most widely used IUDs are configured as flat T-shaped devices (FIG. 1b) that minimize forcible contact between the IUD and the relaxed uterine walls although its 3 pointed sharp edges may sting and irritate the contracting walls. Although such a design is effective in preventing pregnancies, it can lead to perforation, malposition and expulsion since any device-stabilizing forces provided by the relaxed uterine walls are substantially reduced during uterine contractions.

In addition, due to its flat T-shaped design, presently used IUDs are difficult to deliver and may cause tissue wall perforations during insertion because of forward arrow like motion when coming out of the insertion device.

In order to solve these problems of flat IUDs, the present inventors described in a previous application (US20110271963) a three-dimensional IUD which is formed from a single wire during delivery into the uterine cavity and is capable of contracting and expanding along with uterine wall movement while assuming a substantially flat configuration when the uterus is in a relaxed state.

Experiments conducted with this breakthrough design have shown a reduced incidence of migration and a high level of comfort among tested subjects. Although this design was shown to be less susceptible to migration than flat IUDs, improvements to the device that increase device stability in the uterus, especially when relaxed were pursued.

While reducing the present invention to practice, the present inventors unexpectedly discovered that a device which is not completely flattened by the relaxed uterine walls but rather applies a slight counterforce to the uterine walls is less likely to migrate, malposition and expel from the uterus. Without being bound to a theory, the present inventors suspect that a completely flattened device composed of a single (multi-loop) wire is susceptible to 'device creeping' caused by movement of the relaxed uterine walls.

To address this problem, the present inventors have designed a three dimensional device which is characterized by a specific crush force and diameter range that prevent the device from completely flattening under the forces applied by the walls of a relaxed uterus while enabling the device to contract and expand along with an active uterus.

As is further described in the Example section which follows, these characteristics provide the present intrauterine device with substantial advantages over the device described in US20110271963, especially with respect to device stability.

Thus, according to one aspect of the present invention there is provided an intrauterine device. As used herein "an intrauterine device" refers to any device implantable within the uterine cavity, preferably via delivery through the vaginal cavity and cervix. As is further described herein, such a device is preferably configured for releasing an active agent capable of preventing pregnancy (contraceptive or birth control IUD) or treating a uterine disorder such as menorrhagia or medical or surgical therapy to endometrium or myometrium for any length of time including minutes, hours, days, weeks, months or years.

The present device includes a wire having a portion capable of forming an elastically deformable three dimensional structure.

The wire can be composed of an elastic material selected capable of being pre-shaped into the three dimensional structure and being linearized by a pulling force on the ends of the wire. Such a transition between three dimensional and linear configurations can be effected repeatedly due to the elastic nature of the material and its ability to maintain the three dimensional shape in the absence of any pulling force on the ends of the wire (e.g. shape memory).

Examples of materials suitable for such purposes include alloys such as stainless steel, nickel-titanium, copper-aluminum-nickel and other copper containing alloys or polymers such as polyurethanes, polyols, polyethylene terephthalates and acrylates.

The wire can be 50-100 mm long with the portion forming the three dimensional structure being 50-100% of the overall length (10-100 mm).

The three dimensional structure of the present device is formed by two or more contiguous loops of the wire which are angled with respect to each other. The loops can be 12-18 mm in diameter and are arranged (in a two loop configuration) such that one loop is positioned within the plane of the second loop and is angled 60-120, preferably 80-100 degrees with respect thereto (the angle is measured at the wire portion interconnecting the loops). Thus, the loops form a loop-in-loop structure that 'traps' a roughly spherical volume of 0.9-3.0 $cm^3$ (1-1.5 $cm^3$ preferred) with a surface area of 4.5-10.1 $cm^2$ (6-8 $cm^2$ preferred). Further description of the three dimensional structure and formation of the loops from the linear/linearized wire is provided hereinbelow.

As is described hereinabove, the present device was designed in order to improve the stability of a previous design. In order to provide the requisite stability, the present inventors have uncovered that a wire diameter of 0.3-1.0 mm combined with a device overall diameter of 12-20 mm result in elastic resistance to wall forces of a relaxed uterus and a slight device shape change under such forces, while enabling the device to contract and expand along with an active uterus (and nearly completely flatten under strong contractions). Although the present device applies a counter force to the relaxed uterine walls, such a counterforce does not result in tissue irritation and does not lead to any discomfort.

As is mentioned hereinabove, the present device can be used as a birth control device or as a device suitable for treating a uterine disorder such as menorrhagia, or other endometrial or myometrial disorders.

Thus, the present device can be configured to release a metal ion or a hormone (e.g. progesterone, estrogen, menotropine hormones, LH and/or FSH), antibiotics, anti-inflammatory drugs, silver nitrate and/or other chemicals suitable for preventing pregnancy or treating uterine related disorders and conditions.

The active agent can be released from the wire, a coating disposed thereupon or from structures such as beads disposed on the wire.

For example, in the case of copper, the present device can include copper beads 1.5-6.0 mm in diameter mounted on the wire. The beads can be composed from pure copper, gold or silver or any other metal having contraceptive activity.

Figure 4:
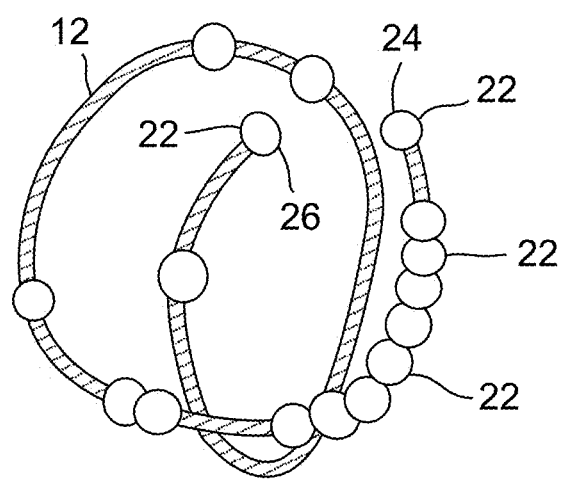
FIG. 4 illustrates a configuration of the device of FIG. 2 which includes copper ion-releasing beads disposed on the wire.

The beads can be threaded over the wire and freely move thereon in which case the beads include a central throughhole (0.4-1.1 mm in diameter), and/or they can be fixed to the wire via an adhesive, or crimping. A configuration of the present device which includes fixed and freely moving beads is illustrated in FIG. 4 which is described in greater detail hereinbelow.

Copper ions can also be released from a copper-containing coating bonded to, or formed on the wire, via, for example, printing, vapor deposition, spray coating and the like.

Hormones such as estrogen, progesterone, menotopins and others can be released from hormone-containing beads or coatings made of hormone-containing polymers such as silicones or polyvinyl alcohol (PVA).

Ablating agents such as trichloroacetic acid, silver nitrate, cantharidin, vitamin A derivatives or other chemically tissue destructive agents can be released from ablating agent-containing beads or coatings. The beads or coatings can include the agent and optionally carrier material. The beads can be fixedly attached to the wire or slidably mounted thereupon.

Figure 1B:
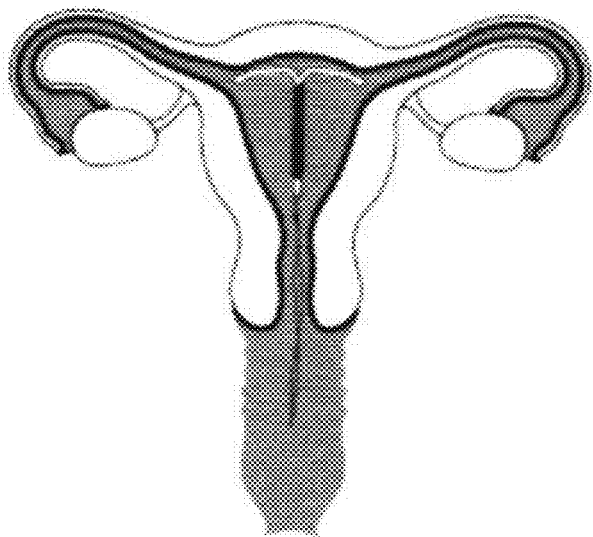
Figure 2:
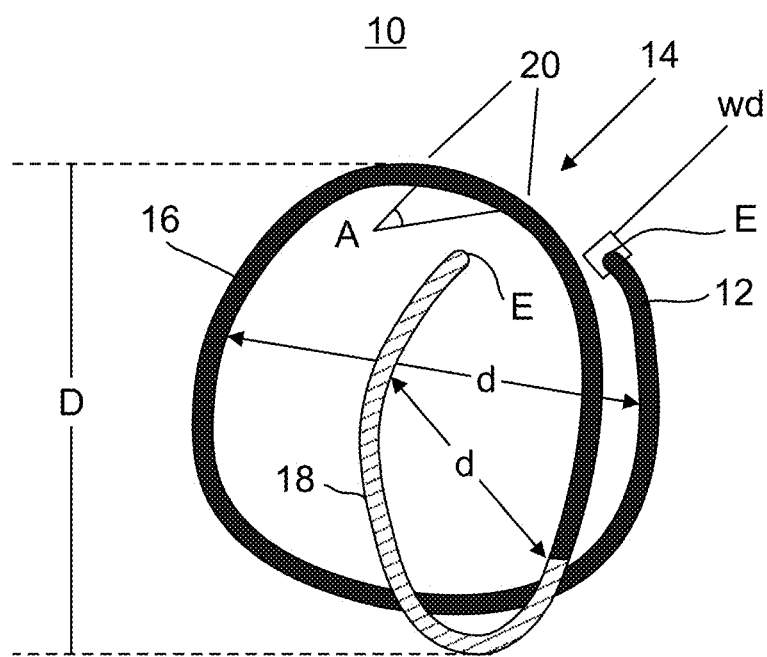
FIG. 2 illustrates the present device in its three dimensional configuration.

Referring now to the drawings, FIGS. 1A-B illustrate one embodiment of the present device which is referred to herein as device 10.

Figure 3:
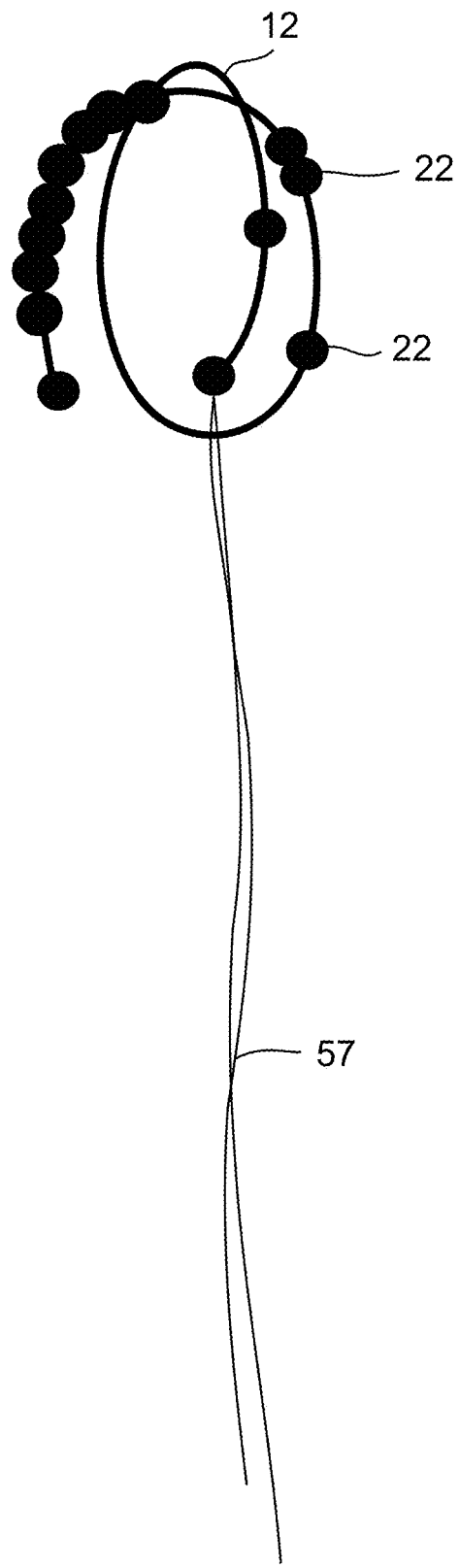
FIG. 3 illustrates the device of FIG. 2 partially compressed by the forces of the relaxed uterine walls.

Device 10 includes a wire 12 forming a three dimensional structure 14 from a first loop 16 contiguous with a second loop 18. The ends of wire 12 (indicated by E) are turned inward in the direction of the volume defined by loops 16 and 18 of device 10. Any of ends E can be connected to a pull string 57 (FIGS. 3 and 5) for loading device 10 into a delivery guide and for removing device 10 from the body. Such a pull string can be fabricated from nylon, polypropylene or polyethylene attached to wire 12 via gluing crimping etc. The function of pull string 57 is described hereinbelow.

Loops 16 and 18 are connected via a contiguous segment 20 which forms an angle 'A' between loops 16 and 18; angle 'A' can be 80-100 degrees.

The overall diameter of device 10 (D) can be 12-15 mm, preferably 13 mm. Loops 16 and 18 are substantially of equal diameter (d) of 12-18 mm, preferably 13 mm. The diameter of wire 12 (wd) can be 0.4-1.0 mm, preferably 0.6 mm.

As is mentioned hereinabove, device 10 is configured to partially compress under the forces applied by the walls of a relaxed uterine cavity.

For example, a device 10 having an overall diameter of 13 mm constructed from a Nitinol wire (0.5 mm in diameter) formed into two contiguous loops (13 mm in diameter) an angled at 90 degrees with respect to each other would partially collapse under a force of 13.6 grams/cm$^2$ to form a roughly oval shape (FIG. 3) with a height of 10 mm. When partially collapsed, device 10 applies an elastic counterforce to the walls of the uterine cavity thus firmly securing device 10 in position. Near flattening of this configuration of device 10 would require about 50-60 grams/cm$^2$.

Collapse of device 10 under such forces is influenced by two separate or combined mechanisms, change in angle A (elastic bending at segment 20) and shape change (round to oval) in each of loops 16 and 18 (elastic bending of the loops).

Collapse along one axis of device 10 is primarily mediated by segment 20 which can bend under relatively lower forces (exerted by relaxed uterine walls). Such collapse enables device 10 to assume the oval-shaped configuration described above. Collapse along other axis requires a larger force (uterine contractions) since it necessitates a shape-change (round to oval) in loops 16 and 18 (as well as further bending of segment 20). Collapse through a combination of axis is also possible and will depend on the orientation of device 10 in the uterine cavity and type of contractions.

FIG. 4 illustrates a configuration of device 10 which includes beads 22 disposed over wire 12. As is mentioned hereinabove, beads 22 can be fixed to, and/or they can freely move upon wire 12. In the configuration shown in FIG. 4, beads 24 and 26 are fixed to ends of wire 12, while the beads 22 in-between freely move along wire 12.

Fixing beads 24 and 16 while allowing beads 22 (in-between beads 24 and 26) to freely slide upon wire 12 provides several advantages. Beads 24 and 26 protect (and blunt) the ends of wire 12 thus minimizing the chances of tissue perforation during delivery and precludes any sharp edges from irritating or piercing tissue during the course of use.

Allowing beads 22 (in-between beads 24 and 26) to freely slide on wire 12 optimizes contact between beads 22 and the uterine wall thus maximizing contact between the active agent contained therein and the tissue wall as well as reducing potential irritation that may be caused by a stationary bead during the course of use.

In addition, since device 10 periodically contracts and expands, beads fixed along wire 12 might snag on one another and interfere with device expansion or contraction. By allowing beads 22 to slide along wire 12, the chances of bead-snagging are reduced. This is particularly important when device 10 is removed, since linearization of the wire can be hampered by bead snagging.

Device 10 can be fabricated by winding a wire (e.g. Nitinol) around a mold (e.g. mandrel) capable of maintaining the wire in the desired form. The mold and wound wire are then heated or chemically treated for a specified time to set the wire in the molded shape and the shaped wire is removed from the mold. The formed wire structure can then be coated and/or beads can be threaded thereupon with a leading and trailing bead permanently attached to the wire via soldering. Any excess wire protruding past the leading or trailing bead can then be trimmed.

As is mentioned hereinabove, device 10 is implanted in the uterine cavity to release an active agent therein.

Delivery and implantation of device 10 in the uterine cavity is preferably carried out using a dedicated delivery guide.

Figure 5:
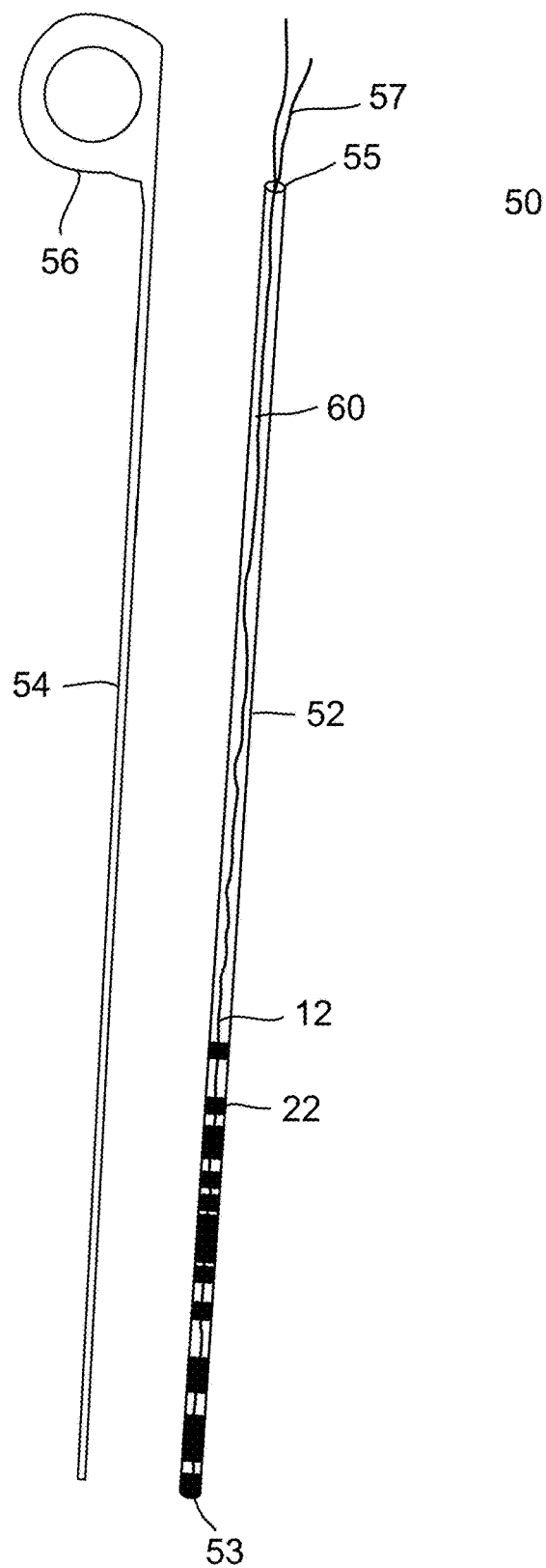
FIG. 5 illustrates a delivery guide utilizable for delivering the present device into a uterine cavity.

FIG. 5 illustrates one configuration of such a delivery guide which is referred to herein as guide 50.

Guide 50 includes a hollow tube 52 having a distal opening 53 and a proximal opening 55 defining a lumen therebetween. Wire 12 with mounted beads 22 and attached pull string 57 is linearized and positioned within the lumen of tube 52. Device 10 can be loaded into the lumen by threading pull string 57 into lumen and pulling it through thereby linearizing the three dimensional structure formed by wire 12 as it is pulled into the lumen. A typical pulling force required for such linearization can be 100-150 grams.

Guide 50 also includes a plunger 54 having a shaft 58 fitted with a handle 56. Plunger shaft 58 fits into the lumen of tube 52 through proximal opening 55. Handle 56 is used to advance shaft 58 within the lumen of tube 52 thus advancing wire 12 with fitted beads 22 out of distal opening 53 incrementally forming the two-loop three dimensional structure of the present device.

Figure 6A:
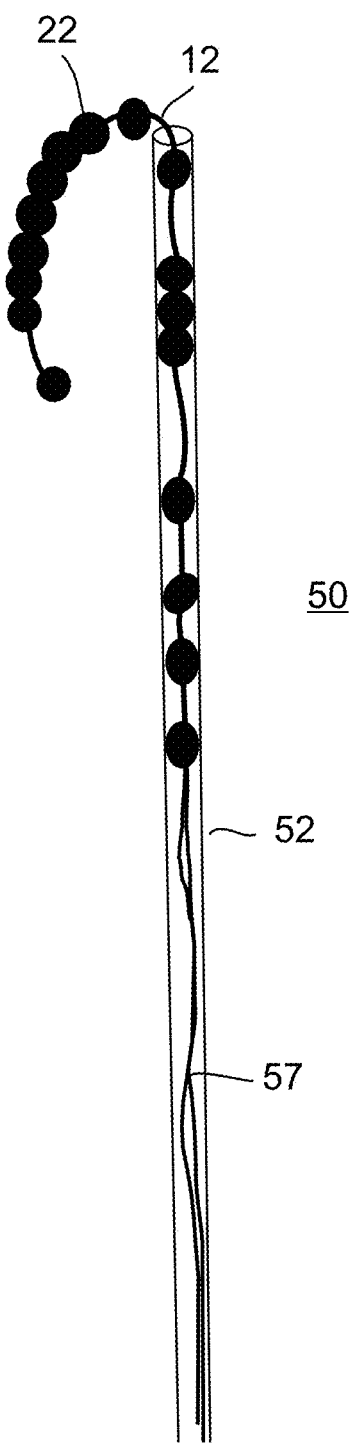
FIGS. 6a-c illustrate stepwise formation of the three dimensional structure of the present device as it is pushed out of the delivery guide in the uterine cavity.
Figure 6B:
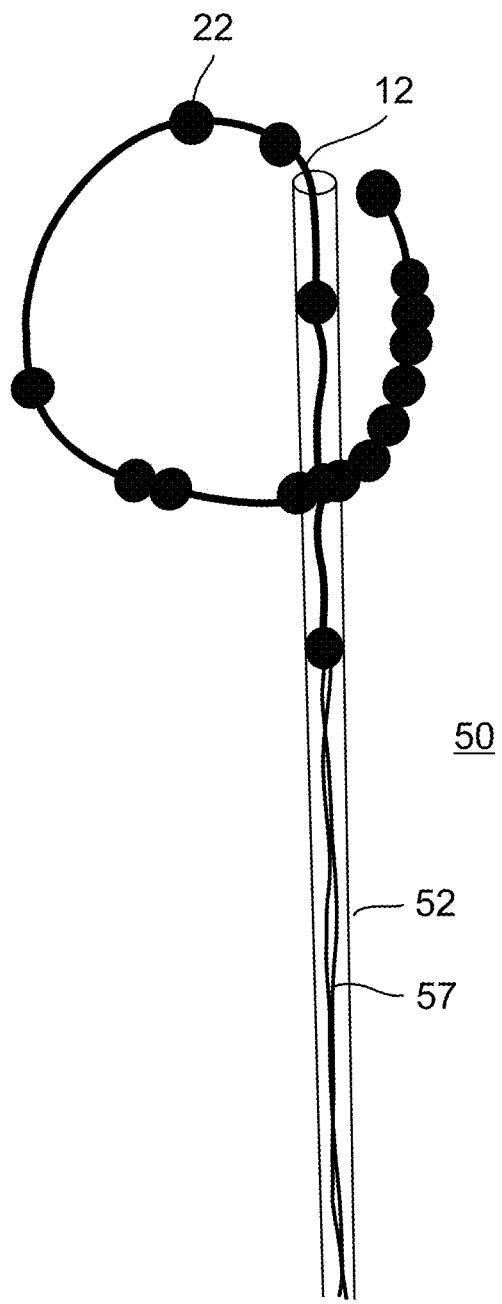
Figure 6C:
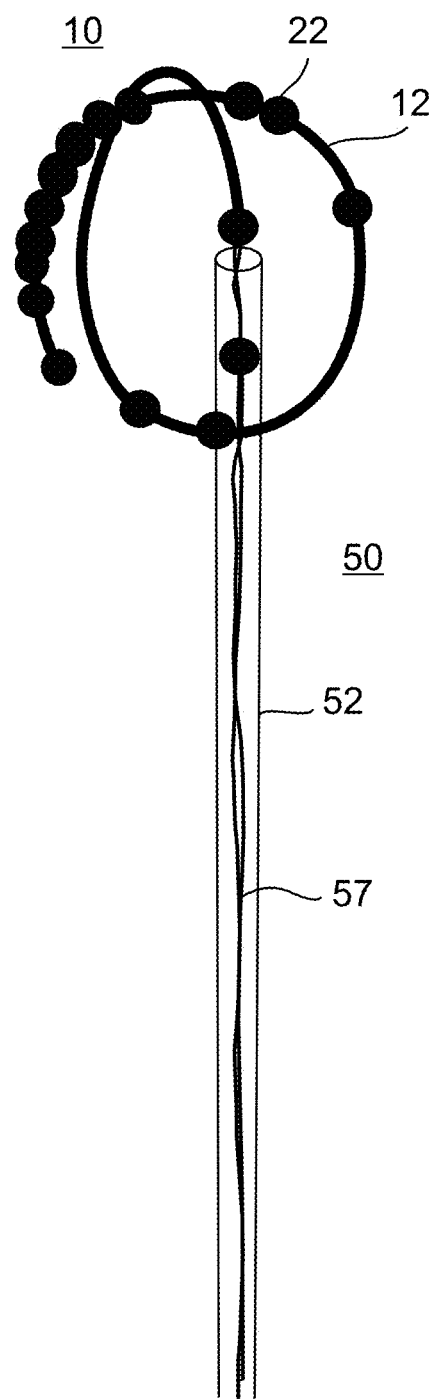

FIGS. 6a-c illustrate delivery of device 10 into a uterine cavity using delivery guide 50.

Distal opening 53 of guide 50 is positionable in the uterine cavity by measuring uterine depth prior to insertion using a hysterometer (sound). The measured depth from the fundus to the external ostium of the cervical canal is marked on tube 52 as reference to the insertion depth of guide 50.

Plunger 54 (not shown in FIGS. 6a-c) is then used to advance wire 12 and attached beads 22 out of distal opening 53 as is shown in FIGS. 6a-c, thereby forming the first loop (FIG. 6b) and contiguous second loop (FIG. 6c) of the 3D structure of device 10 from the linear wire. Delivery guide 50 is then removed from the body leaving behind device 10 in the uterus and attached pull string 57, the proximal end of which is positioned at the vaginal canal.

Delivery guide 50 can also include an attached light source (e.g. LED or fiber optic light) in order to illuminate the uterine cavity with white light or light of a specific wavelength (e.g. blue light). Delivery guide can also include a camera for imaging the uterine cavity in 3D instead of using a hysteroscope.

As used herein the term "about" refers to ±10%.

Additional objects, advantages, and novel features of the present invention will become apparent to one ordinarily skilled in the art upon examination of the following examples, which are not intended to be limiting.

EXAMPLES

Reference is now made to the following examples, which together with the above descriptions, illustrate the invention in a non limiting fashion.

Example 1

A clinical study employing an IUD device based on the teachings of US20110271963 was initiated in January of 2014. The study included fifty female subjects, 1 post-abortive, 39 with heavy menses, and 44 nulliparous.

Three month follow-up data for 29 of the 51 test subjects was obtained and analyzed. Ten cases of expulsions were reported. There were no reports of pregnancies, perforation or malposition. Of the 29 monitored subjects, 19/29 reported being "very happy" and 9/29 "somewhat happy".

While the study has no comparative arm and offers a limited basis for analysis it was observed that there could potentially be an expulsion issue. In order to address this issue, the TUB was modified as described herein to improve the performance of the device in-situ. Design changes included increasing the frame diameter by 30% from 10 mm to 13 mm and increasing the rigidity of the frame by increasing the wire diameter by ~30% from 0.335 to 0.432 to further reduce malleability which in turn should aid in better positioning.

Example 2

Multi-Center Study

A multi-center study was conducted in order to test the expulsion and pregnancy rate as well as the number of malposition incidents of the present device. The number of patients varied between 15 and 220 and included women aged 15 to 42 who met specific inclusion and exclusion criteria and who were in need of long acting reversible contraception.

Table 1 below summarizes the findings.

TABLE 1 clinical data collected from four studies using the present device

| Study Group | Insertions | Expulsions | Expulsion rate | Pregnancies | Pregnancy rate | Malposition |
|---|---|---|---|---|---|---|
| A | 15 | 0 | 0 | 0 | 0 | 0 |
| B | 50 | 10 | 20% | 0 | 0 | 0 |
| C | 220 | 5 | 2.2% | 1 | 0.45% | 0 |
| D | 200 | 8* | 5% | 0 | 0 | 0 |
| Total | 485 | 23 | 4.7% | 1 | 0.2% | 0 |

*Six of eight expulsions seen with the same physician, caused by what appears to be a non-advised insertion technique of withdrawing the tube 1.5 cm before deploying the device. Corrective training action has been taken.

Overall data appears to meet or improve on published adverse event rates. Expulsion rate in study group B is related to poor candidate selection (more than half suffering menorrhagia and dysmenorrhea at baseline) and employment of an unusually aggressive insertion technique. Nearly all expulsions were with young nullips and post-abortion patients.

QOL parameters, i.e. satisfaction, lack of pain and bleedings appear equivalent or better than expected for all groups including study group B. Overall the results with the present device are promising.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:
1. An intrauterine device comprising:
    a wire having free ends;
        wherein the wire comprises a plurality of beads attached to the wire;
        wherein the plurality of beads:
            a) are 1.5-6.0 mm in diameter;
            b) configured to freely slide upon the wire; and
            c) comprise an active agent;
    a delivery guide;
        wherein the wire is configured to be deliverable from the delivery guide;
        wherein the delivery guide is configured to maintain the wire in a linear configuration;
        wherein a portion of the wire is configured to form a three dimensional structure based on the wire being advanced out of the delivery guide;
        wherein the three dimensional structure:
            a) is configured to be elastically deformable to a partially collapsed configuration;
            b) has a crush force of at least 15 grams/cm$^2$; and c) is configured to elastically contract and expand in response to contraction and expansion of the uterine cavity.

2. The device of claim 1, wherein the three dimensional structure is formed by at least two loop-shaped structures angled with respect to each other.

3. The device of claim 2, wherein an angle between the at least two loop-shaped structures decreases when the three dimensional structure elastically contracts.

4. The device of claim 3, wherein at least one of the at least two loop-shaped structures is configured to elastically ovalizes when the three dimensional structure elastically contracts.

5. The device of claim 2, wherein the at least two loop-shaped structures are positioned at an angle of 80-100 degrees with respect to each other.

6. The device of claim 2, wherein each of the at least two loop-shaped structures is 12-14 mm in diameter.

7. The device of claim 1, wherein the wire is coated with a material capable of releasing an active agent in the uterine cavity.

8. The device of claim 7, wherein the active agent is selected from the group consisting of a hormone, a tissue ablation agent, a chemical agent and pharmaceutical agent.

9. The device of claim 1, wherein the three dimensional structure is 13-20 mm in diameter.

10. The device of claim 1, wherein the wire of the three dimensional structure is configured to be elastically linearizable via a pull force of 100-150 grams (gf) to a free end of the wire.

11. The device of claim 1, wherein the wire is 0.4-0.6 mm in diameter.

12. The device of claim 1, wherein the wire is made of Nitinol.

13. The device of claim 1, wherein the beads are spaced apart along the wire forming the three dimensional structure.

14. The device of claim 1, wherein the beads are made of copper.

15. The device of claim 1, wherein the active agent is selected from the group consisting of a hormone, a tissue ablation agent, a chemical agent and pharmaceutical agent.

* * * * *